(12) United States Patent
Dimitrijevic

(10) Patent No.: US 9,218,569 B2
(45) Date of Patent: Dec. 22, 2015

(54) RULES-BASED MANAGEMENT SYSTEM AND METHOD FOR PROCESSING MEDICAL INFORMATION

(71) Applicant: Biljana Dimitrijevic, Erlangen (DE)

(72) Inventor: Dejan Dimitrijevic, Erlangen (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 302 days.

(21) Appl. No.: 13/852,137

(22) Filed: Mar. 28, 2013

(65) Prior Publication Data

US 2014/0279807 A1  Sep. 18, 2014

Related U.S. Application Data

(60) Provisional application No. 61/781,153, filed on Mar. 14, 2013.

(51) Int. Cl.
*G06F 17/00* (2006.01)
*G06N 5/02* (2006.01)
*G06F 17/30* (2006.01)
*G06F 19/00* (2011.01)

(52) U.S. Cl.
CPC ............... *G06N 5/025* (2013.01); *G06F 17/30* (2013.01); *G06F 19/345* (2013.01)

(58) Field of Classification Search
None
See application file for complete search history.

(56) References Cited

U.S. PATENT DOCUMENTS

| | | | |
|---|---|---|---|
| 7,660,777 B1* | 2/2010 | Hauser | 706/45 |
| 7,720,826 B2* | 5/2010 | Fitzer et al. | 707/694 |
| 8,805,483 B2* | 8/2014 | Morganroth | 600/509 |
| 2007/0016544 A1* | 1/2007 | Graefe et al. | 707/1 |
| 2008/0312959 A1* | 12/2008 | Rose et al. | 705/2 |
| 2011/0231353 A1* | 9/2011 | Wang et al. | 706/45 |
| 2013/0041921 A1* | 2/2013 | Cooper et al. | 707/780 |
| 2013/0185099 A1* | 7/2013 | Bucur et al. | 705/3 |

* cited by examiner

*Primary Examiner* — Kakali Chaki
*Assistant Examiner* — Luis Sitiriche
(74) *Attorney, Agent, or Firm* — Harness, Dickey & Pierce, P.L.C.

(57) ABSTRACT

A rules-based management system includes a rule repository to store a plurality of rules relating to medical information, a rule query language engine to generate a query based on a received signal and to search the rule repository based on the query, and a rule processing engine to formulate an instruction based on one or more rules produced by the search of the rule repository and to generate a signal based on the instruction. The system further includes an interface to a cloud network connected to a plurality of doctors, nurses, technicians, and/or other personnel or patients.

18 Claims, 9 Drawing Sheets

Cloud Computing

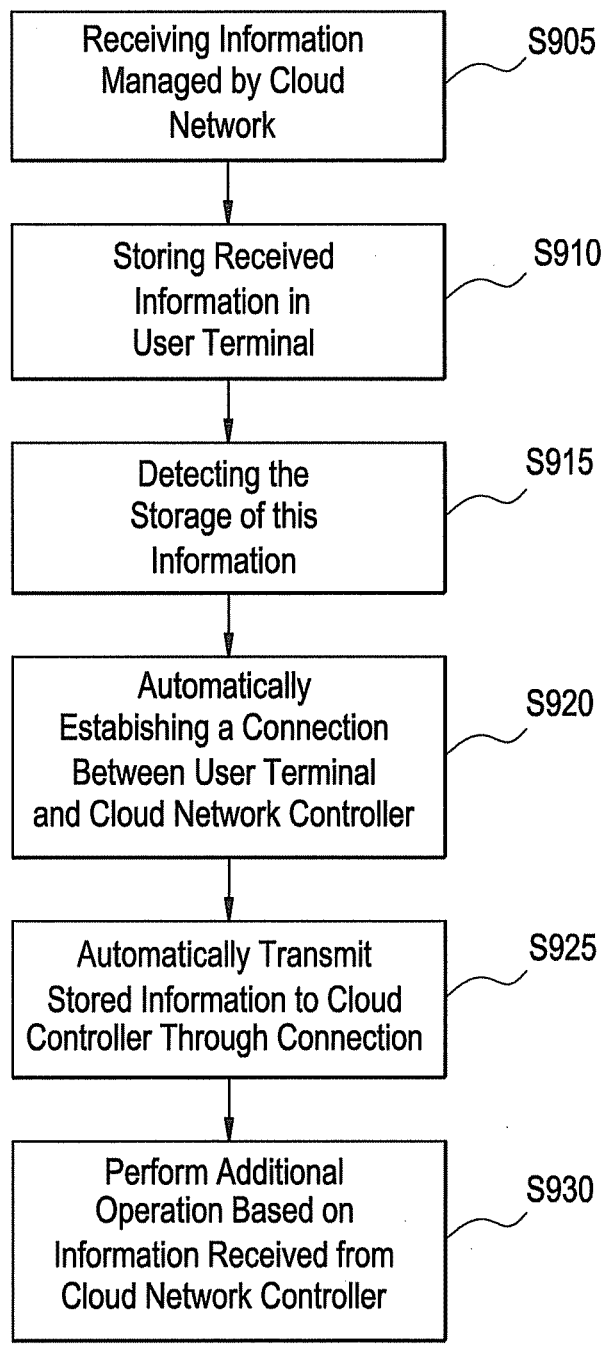

RULES-BASED MANAGEMENT SYSTEM AND METHOD FOR PROCESSING MEDICAL INFORMATION

BACKGROUND

1. Field

One or more embodiments relate to managing information.

2. Related Art

Various networks have been developed for exchanging information between health care professionals. These systems implement legacy algorithms that do not perform information transfers on the real- or near real-time basis required by doctors in providing quality health care decisions. Also, these systems provide low-level messaging which fail to satisfy the complex, data-intensive, and time-sensitive demands desired in a modern day hospital practice and administration.

SUMMARY

In accordance with one embodiment, a rules-based management system is provided which uses artificial intelligence and/or other algorithms to control the transfer, storage, access, and dissemination of medical information in a variety of health care applications.

In accordance with another embodiment, a rules-based management system which controls the transfer, access, and dissemination of medical information through a cloud network, and which processes that information based on a variety of cloud-computing algorithms used to implement or operate with the rules-based management system.

In accordance with one embodiment, a rules-based management system comprises a rule repository configured to store a plurality of rules relating to medical information, a rule query language engine configured to generate a query based on a received signal and to search the rule repository based on the query, a rule processing engine configured to formulate an instruction based on one or more rules produced by the search of the rule repository and to generate a signal based on the instruction, and an interface to a cloud network. The interface may be configured to send the signal to the cloud network to enable performance of a task related to the medical information.

In accordance with another embodiment, a method for processing information comprises generating a query for a rule repository, searching the rule repository based on the query to locate one or more rules relating to medical information, formulating an instruction based on the one or more rules, generating a signal to perform a task based on the instruction, and establishing a connection with a cloud network for transmission of the signal, wherein the task corresponds to medical action to be performed in a hospital.

BRIEF DESCRIPTION OF THE DRAWINGS

FIG. 9 shows operations included in another embodiment of a rules-based method for managing medical information.

DETAILED DESCRIPTION

Figure 1:
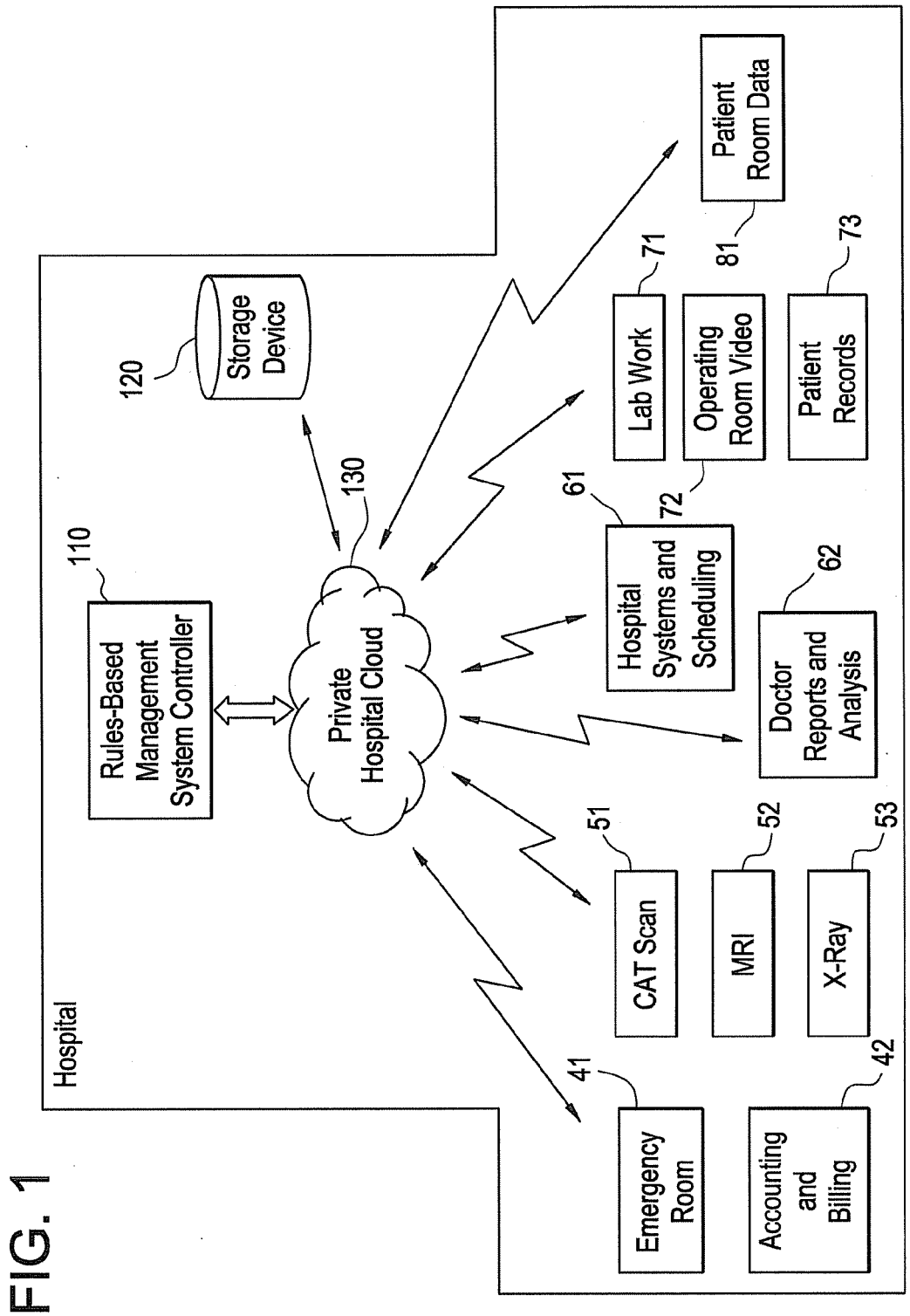
FIG. 1 shows an embodiment of a rules-based management system for managing medical information.

FIG. 1 shows an embodiment of a rules-based management system which includes a rules-based management system (RBMS) controller 110, a storage device 120, and a network 130. The system is shown as being applied in a hospital environment; however, in other embodiments the system may be applied to a clinical setting, doctor's office, outpatient facility, and/or another environment related to the medical field or industry.

The controller 110 receives signals that are internally generated in the system, for example, as a result of a scheduling program and ones that are received by one or more user terminals connected to the controller through the network. The signals may be task requests, test results, patient data, or other information related to hospital administration and care. As will be described in greater detail, the controller operates according to one or more software modules dedicated to performing operations of the rules-based management system.

The storage device 120 stores information for the software modules and medical information to be used by care professionals for hospital patients, as well as other information related to the generation and transmission of data to and from the network as will be described in greater.

The network 130 may be any network for transmitting information. In accordance with one embodiment, the network corresponds to or includes a cloud network. The network may be a private cloud accessible only to authorized personnel in, for example, the administration of health care services. However, in other embodiments, the network may include portions that are available to non-authorized users and/or other segments of the public.

The rules-based management system controller 110 may be electronically coupled to a variety of hospital areas and subsystems. These systems include emergency room systems 41 such as patient monitoring devices, electronic reports generated by nurses and doctors, information based on communications with in-coming ambulances or care to be given by paramedics at remote patient locations, and admission and other information.

Another system manages information for the accounting and billing department of the hospital. This information includes patient data and insurance company and financial data. The accounting and billing systems may store information corresponding to cost invoices generated to order supplies, patient bills (whether delinquent or not), compensation, and statistical analysis on the financial performance of the hospital.

Another system manages information generated by the imaging department of a hospital. This information may include, for example, CAT scan data 51, MRI data 52, X-ray machine images 53, and ultrasound images.

Other systems manage data for hospital systems and scheduling 61 and for the generation, storage, and dissemination of medical records, reports, and patient charts 62. Other systems manage the storage and dissemination of laboratory results and diagnostics 71, operating room video 72, and patient records generated at various locations inside and outside the hospital 73. Other systems manage data 81 collected in the rooms of admitted patients such as intermittent blood pressure readings, electrocardiograms, temperature, and other vital signs or care/life-support data.

Figure 2:
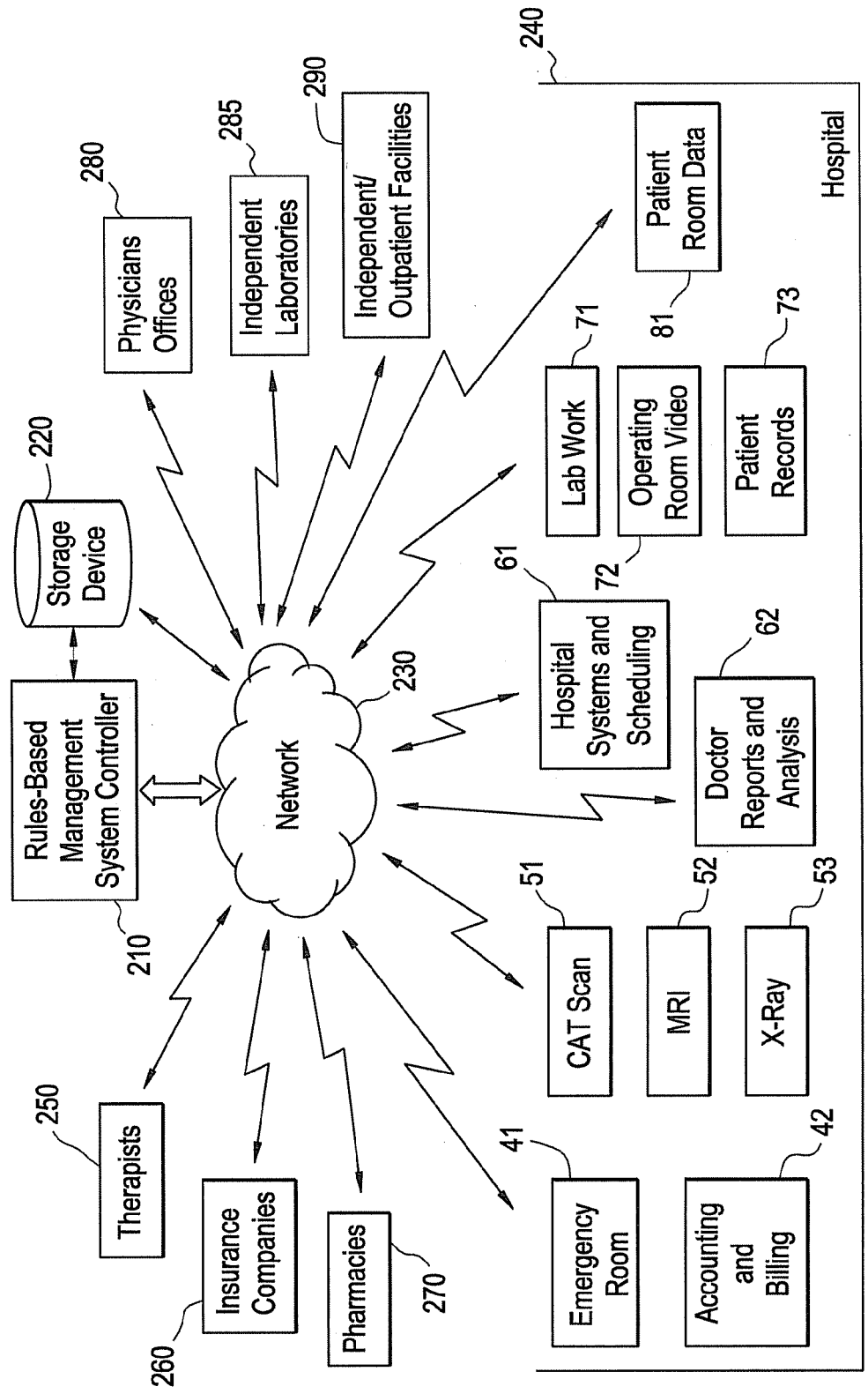
FIG. 2 shows another embodiment of a rules-based management system for managing medical information.

FIG. 2 shows another embodiment of a rules-based management system which includes a rules-based management system (RBMS) controller 210, a storage device 220, and a network 230 which may be similar in structure to the controller, storage device, and network shown in FIG. 1. Also, the RBMS controller is connected to the same systems of a hospital 240 as in the previous embodiment. However, the embodiment of FIG. 2 differs in that the rules-based management system controller 210 is connected to networks, entities, and/or terminals outside of the hospital.

More specifically, as shown in FIG. 2, the RBMS controller 210 may be connected to one or more of a therapist network or terminal 250, a plurality of insurance company networks or terminals 260, a plurality of pharmacy networks or terminals 270, multiple physician offices 280, a plurality of independent laboratory networks or terminals 285, and a plurality of independent or outpatient surgical or other facility networks or terminals 290. Although FIG. 2 shows all communications going through network 230, in other embodiments the RBMS controller may communicate with the aforementioned terminals through other networks or a hybrid network. Also, the types of information to be stored in storage device 220 may be enhanced given the broadened scope of communications to be performed by controller 210.

Figure 3:
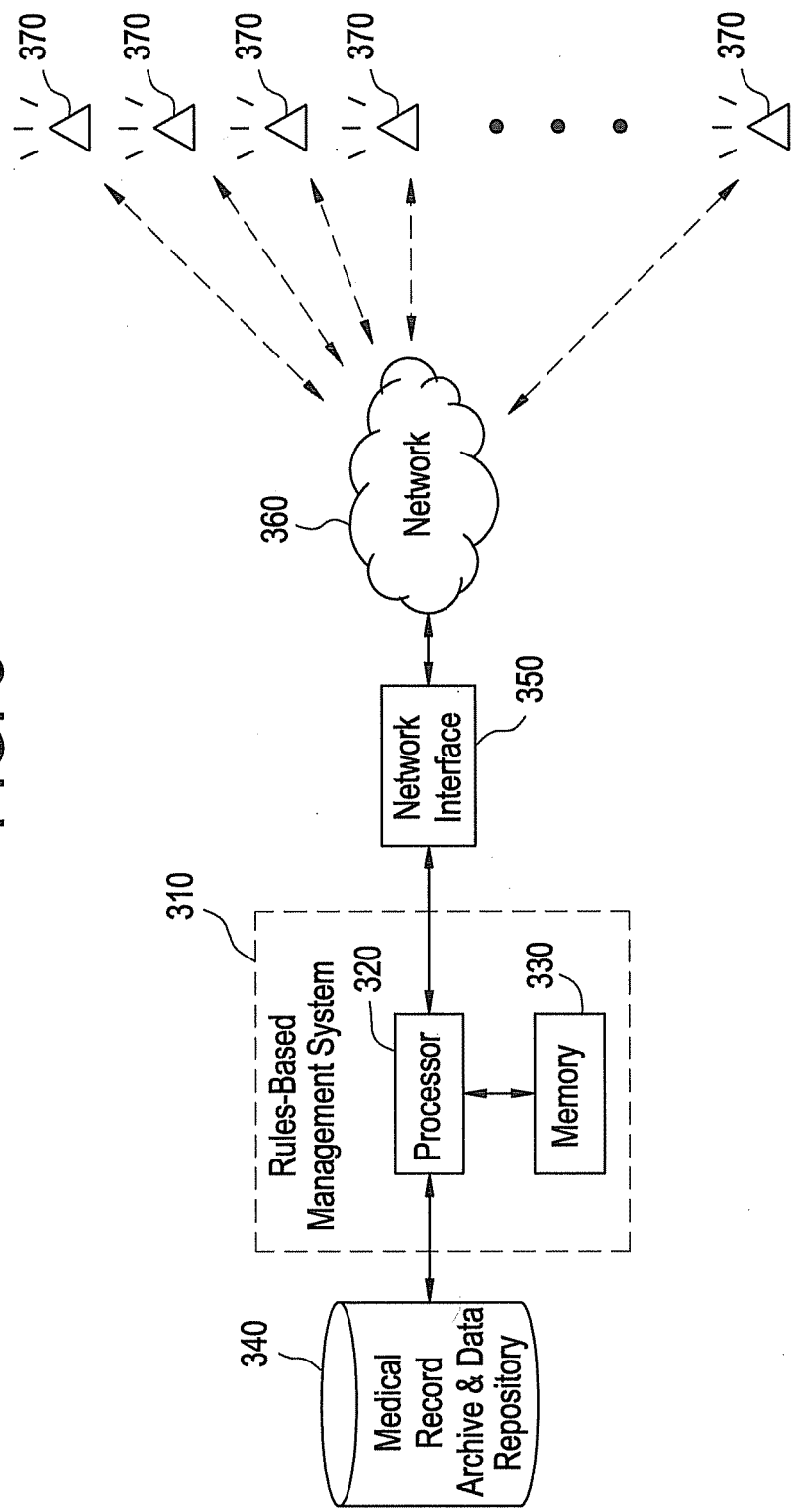
FIG. 3 shows an example of the structure and operation of a rules-based management system as described herein.

FIG. 3 shows an example of an operational environment for the RBMS controllers described in accordance the aforementioned embodiments. As shown in FIG. 3, the system shows RBMS system 310 formed to include a processor 320 and a memory 330.

The processor 320 may be any processor capable of implementing the software modules and other functions of the controller described herein, as well as to handle communications through one or more networks including a cloud network to be described in greater detail. Thus, in one embodiment, processor 320 may be referred to as a cloud-computing processor, however the processor may have additional functionality.

The memory 330 may store the control programs, applications, scripts, middleware, firmware and other code for implementing the software modules and other functions of the processor.

A database 340 or other information storage device stores information similar to that stored in devices 120 and 220. As previously indicated, this information includes medical records, patient data and imaging information, financial records and other information to be archived.

A network interface 350 physically couples the RBMS system to a network 360, but also places the data and other information to be exchanged through the network in a compatible protocol. While only one interface is shown, in other embodiments multiple interfaces are shown to communicating with different networks, which include any combination of local and/or wide area networks, wireless and/or wired networks, public and/or private network.

The network 360 may be any one or more types of networks are previously indicated. In one embodiment, the network is a cloud network and in this case processor 320 is a cloud network controller operating, for example, based on communication control programs stored in memory 330.

As shown in FIG. 3, the RBMS system 310 communications with a plurality of access points 370 through the network. Each access point includes an interface for allowing the RBMS system to communication with respective terminals or networks associated with the access points. One of the access points may correspond to a mobile terminal (e.g., smart phone, tablet, portable computer, etc.) used, for example, by a doctor or patient. Other access points may include a modem or other interface circuit for allowing the RBMS system to communication with a network of an insurance company or pharmacy or any of the other entities previously described.

The access points 370 are shows to be wireless access points. When used in a local application (e.g., inside a hospital), the access points may be Wi-Fi hot spots, Bluetooth transceivers, or other short-range communication interfaces. When used outside the hospital, the access points may be pico or femto cell controllers, base stations in a mobile communication network, or even satellite transceivers. One or more of the access points may communicate with the RBMS through one or more land-lines including the internet or fiber-optic cables.

Figure 4:
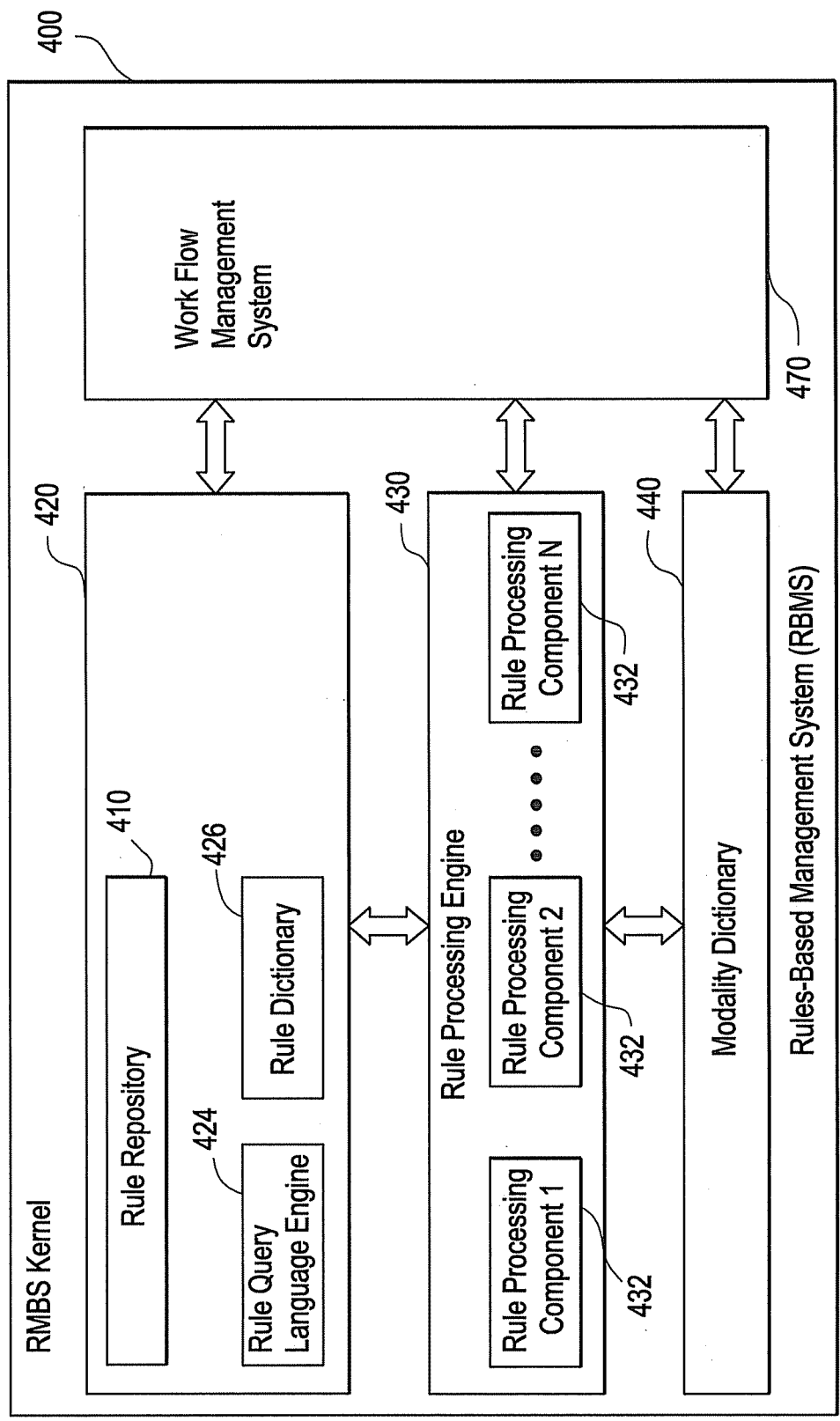
FIG. 4 shows software modules included in one embodiment of a rules-based management system.

FIG. 4 shows an embodiment of the rules-based 400 management system which includes a plurality of software modules. The software modules include a rule repository 410, a rules-based management system kernel 420 (which may or may not include the rule repository), a rule processing engine 430, and a modality dictionary 440. The software modules may be arranged or otherwise implemented in a variety of processing architectures. Examples include a rules-based processing engine (as shown), a virtual machine, neural network, an expert system, and/or software implementing various types of artificial intelligence algorithms, or a combination thereof.

The rule repository 410 stores a plurality of rules to be used in performing an action by the system. The rules are stored in a database (e.g., a relational database), a distributed system of interconnected databases, and/or other storage devices or information management systems. The rules are written to help implement, constrain, or manage various actions or activities to be taken by the system. In one embodiment, the rules are partitioned into categories.

In a hospital application of the system, one category may correspond to accounting and billing to be performed by the hospital. For example, the rules in this category may define the conditions under which a patient is to be billed for emergency room services, outpatient procedures, lab work, hospital room charges, medical equipment, insurance coverage, therapy, medical diagnostics, drug and prescription care and/or various other billing-related activities.

Another category may correspond to medical record management in the hospital. For example, the rules in this category may define the conditions under which medical images are to be archived or retrieved for analysis by doctors on a per-patient basis, medical history information is to be stored, retrieved and distributed to various offices and personnel, legal procedures are to be implemented to ensure the privacy of patient records, the writing and authorization of prescriptions for patient care, the exchange of records and other information with primary care doctors and specialists outside the hospital, access to medical tests from independent laboratories, as well as other medical record management.

Another category may correspond to managing the performance of laboratory work within the hospital. For example, the rules in this category may define when certain lab work is required based on doctor orders or diagnosis, the type and nature of that lab work, the scheduling of the lab work and the subsequent distribution of that lab work to technicians and doctors for performing patient care.

Another category may correspond to patient monitoring in the hospital. For example, the rules in this category may manage patient status in the emergency room, during post-operative care, intensive care, and in-room vitals and the real-time and/or subsequent dissemination and recording of this information to health care professionals. Additional rules may manage the tracking of patients in the hospital as well as verifying patient identity and confirming patient conditions and procedures to be performed and care to be given. This tracking function may prove especially helpful when individuals under police custody are in the hospital.

Another category may correspond to managing the schedules of specific doctors. For example, the rules in this category may specify to which patient rooms doctors are to be assigned in an emergency room. Other rules may manage doctor appointments and schedules and still other rules may track the location of doctors within the hospital and/or their in-route status.

Another category may manage or otherwise track the arrival of patients by ambulance and/or may control communications between heath care professionals in the hospital and paramedics, for example, giving care at the scene of an accident or in an ambulance. These rules may also manage the recording of conversations and/or other instructions given at this time, which records are to be archived for subsequent medical and/or legal review.

Another category may correspond to the scheduling, performance and/or subsequent archival and dissemination of medical imaging and/or other diagnostic or exploratory medical tests. For example, the rules in this category may schedule the performance of CAT scans, MRIs, and X-rays under the authorization of a doctor. The rules may also control the priority of importance of scheduling imaging procedures relative to other patients. For example, a patient who has had a cardiac event may be given higher priority over a patient with a broken bone.

Other categories of rules may manage information, activities, communication of information, and/or interactions relating to the hospital and/or other medical facilities and personnel. For example, rules may be included to manage communications among the hospital, doctors, technicians, patients, agencies, insurance companies, and/or pharmacies to name a few.

One of these categories of rules specifically relates to communications performed in a cloud-based network. In such an application, a cloud network controller control the receipt, transmission and storage of information throughout the various authorized entities and users of the cloud based, in part, on the rules stored in the rule repository. The cloud may be a private cloud, a public cloud, or a combination of both. In this latter case, communication is controlled to prevent private information from being transferred to the public cloud, in order to, for example, protect patient privacy.

One set of rules may relate to the registration of users of the cloud. For example, some rules may control the terms of registration. Other rules may control identity confirmation and authentication of personnel. Other rules may control the classification of users into different groups with different permissions and/or access to information on the cloud. For example, doctors may be given access to more and/or different types of information than technicians or patients.

Other rules may control the manner or conditions under which information is to be received from or transmitted to different user terminals. Other rules may control the manner or conditions under which information is to be stored in a network-attached storage device, storage area network, relational or other database, and/or another type of storage or archival device.

Other rules may control the scheduling of notifications, messages, paging signals, and/or transmission of data to and from a network corresponding to the cloud. This may be controlled, for example, by the cloud network controller. The cloud network controller may be a processor located at a network entity such as a server or other network management device. In one application, the cloud network controller may control timing and other conditions under which information is to be transmitted to or between registered cloud terminals.

Additionally, or alternatively, the repository rules may be categorized into various classes. For example, one class of rules may relate one or a group of rules to one or more other rules. For example, the writing of a prescription may relate or otherwise involve the combination one rule concerning the type of drug to be administered with other rules governing the insurance coverage of that drug based on patent insurance and also the creation of a record documenting the type of dosage of that drug and the frequency with which the drug is to be administered.

Another class of rules may place constraints or limitations on various activities of the hospital including hospital responsibilities and patient care. For example, some rule may limit the period a patient may be admitted to the hospital based on medical conditions and/or insurance coverage. Other rules may generate records for preventing certain drugs from being prescribed based on patent allergies, medical conditions and/or other intolerances. Other rules may place constraints on the publicity or dissemination of information protected by doctor-patient confidentiality and/or other laws or regulations governing the same.

Another class of rules may provide for the conversion of information or data from one form to another. This may involve, for example, automatic report generation, automatically associating one form of information with another to be included in an integrated format, and converting raw medical data into processed data forms for diagnostic analysis. Other rules may consolidate information from different sources that would otherwise have to be collected manually for inclusion into a patient chart or record.

The rules-based management system kernel 420 includes a rule query language (RQL) engine 424 and a rule dictionary 426. The RQL engine performs the function of searching the rules repository for rules that relate to an action or activity to be performed by the system. The RQL engine may perform this function based on certain terms, words, directive, and/or information in data fields included in a search statement corresponding to the action or activity to be performed. As will be described in greater detail, the action or activity may be determined based on a control signal or request received by the system, which may either be automatically generated, for example, in accordance with programming instructions or scheduling and/or in response to instructions entered into the system, for example, by doctors, nurses, technicians or other health care professionals.

In accordance with one embodiment, the RQL engine search operates based on a set of instructions in a query language specifically designed to search for rules in the rules repository. The query language may include instructions for retrieving rules corresponding to search query statements or other directives generated by the system and may also include instructions designed to operate interactively with the rules repository and/or other system modules.

For example, when the system is to schedule, archive, or disseminate information relating to a medical imaging procedure, the RQL engine may generate a query to determine which rule or rules exist for managing such an operation. The query, for example, may first seek to locate rules that govern particular insurance-related conditions for the procedure given hospital policy and or the specific insurance policy of the concerned patient.

Once such a rule has been found and retrieved from the repository, additional queries may be generated to locate more particular rules covering the procedure. These additional queries may seek to retrieve rules for a particular type of imaging procedure to be performed, e.g., magnetic resonance imaging, CT scans, X-rays, etc. Then, queries may be generated to locate more specific rules that apply to the specific type of imaging system. By generating these queries, the RQL engine may therefore filter information from and interactively operate with the rule repository in order to obtain the information needed by the system.

Additionally, or alternatively, the RQL engine may perform a search function based on the conditions or operations of a control program such as in the registration and authentication of cloud-users and control of the communication or storage of information relating to the cloud.

The RQL queries may be written, for example, in a structured query language (SQL), data manipulation language (DML), resource description framework (RDF) language, contextual query language (CQL), extensible markup language (XML) or any one of a variety of other languages for performing database or information searching. In accordance with one embodiment, a proprietary query language based specifically on the architecture and processing operations of the system may be used to search the rule repository.

The RQL engine may generate queries for the rule repository based on one or more search terms obtained, for example, from an activity to be performed by the system or an instruction received by a health care professional or administrator. For example, in the case where the RQL engine generates queries for the rule repository for the retrieval of medical information based on two terms (term 1 and term 2), the following queries are possible.

or higher-level queries into a form suitable for performing an efficient and targeted search of the rule repository.

The rules dictionary 426 stores information corresponding to the rules in the rules repository. In accordance with one embodiment, the rule dictionary may store terms and phrases that are related to the rules in the rule repository. When handling a query, the RQL engine 424 may parse a received instruction or higher-level query or task to be handled by the system and search the rule dictionary for terms or phrases that are used in the rule repository that correspond to the instruction or higher-level query. Also, the rule dictionary may be used to semantically describe the rules in the rule repository using rule dictionary elements. The rule dictionary may therefore assist the RQL engine in locating the most relevant rule for the task or query at hand.

Additionally, or alternatively, the rule dictionary may store information that defines the rules in the rules repository and the relationship between and among those rules in the context of activities to be performed by the system. The rule dictionary may follow or store information to implement a rules policy that governs the system with respect to the storage, management and/or analysis of system specific data, the registration and authentication of cloud users, and the communication of information based on one or more policies implemented by a cloud network controller and its software.

In accordance with one embodiment, the rule dictionary may contain one or a plurality of data models, rule sets, and or links to other rule dictionaries in the system. The rule dictionary, therefore, may introduce flexibility into the system to enable the handling of complex queries and tasks that arise in a hospital or other medical system application.

In one exemplary application, the RQL engine may access the rule dictionary 426 before accessing the rule repository

| | |
|---|---|
| term1 term2 | retrieves documents that contains term1 or term2 (they need not contain both) |
| {term1 term2} | retrieves documents that contains term1 or term2, where they are treated as synonyms of each other (they need not contain both) |
| term1^2.3 | the weight of term1 is multiplied 2.3. |
| +term1 +term2 | retrieves documents that contain both term1 and term2. |
| +term1 − term2 | retrieves documents that contain term1 and do not contain term2. |
| title:term1 | retrieves documents that contain term1 in the title field (Field indexing must be configured to record the title field). |
| term1 − title: term2 | retrieves documents that contain term1, but must not contain term2 in the title field. |
| "term1 term2" | retrieves documents where the terms term1 and term2 appear in a phrase. |
| "term1 term2"~n | retrieves documents where the terms term1 and term2 appear within a distance of n blocks. The order of the terms is not considered. |

In accordance with one embodiment, the RQL engine implements optimization techniques and evaluation strategies to shorten the evaluation time of querying the rule repository. This techniques and strategies may be implemented for example by designing the RQL engine to implement reasoning algorithms in the generation of queries that target in a more effective manner the rule or rules to be retrieved from the rule repository.

The RQL engine may perform these functions based on instructions automatically generated by control software of the system, instructions from a cloud network controller, and/or in response to instructions from health care professionals, e.g., a request for patient medical history. In this situation, the RQL engine may include a translator to translate the instructions or higher-level queries received from the system and/or personnel into a language compatible with the RQL engine, and a parser to parse the translated instructions 410. Such a situation may arise when the RQL engine must convert a task, instruction, or higher-level query received from the system or user to a format compatible with the rule dictionary. In such a case, the RQL engine may convert data to terms that are located in the rule dictionary. Information corresponding to those terms may then be used by the RQL engine to formulate a search query of the rule respository, and the information retrieved from the repository in response may then be used by the rule processing engine to perform a related action or activity.

In addition to the foregoing features, the RQL engine 424 may create new rules to be stored in the rule repository and, commensurately, new definitions for storage in the rule dictionary. This is especially beneficial for purposes of updating the system to changes in hospital rules, insurance and legal regulations, and/or permissions and authorizations of cloud users and the information to be communicated by and through the cloud. In one embodiment, the RQL may create these new rules, for example, based on control software stored in the system and/or scripts or other programs written by system managers based on new or modified data stored for the system. An example of such control software is a Rules Manager provided, for example, by SAP, Oracle, or another database or intelligent system software manufacturer.

Such a Rules Manager, for example, allows for the creation of highly complex rule-based applications, in a relatively short period of time. The Rules Manager may operate using a decision tree and path (network) for rules. A manager of this type may be referred to as knowledge-based intelligent logic or expert system which may operate in four stages: an inference engine (patterns), execution engine (checker, which may or may not be included in the inference engine), working memory (facts), and a knowledge base which may correspond to the rules repository or another rules database. The Rules manager may be implemented by a component of the RMBS kernel 420, by the rule processing engine 430, or another processing logic or module.

The rule processing engine 430 includes a plurality of rule processing components (RPCs) 432, each of which is dedicated to performing different (though possibly related) number of activities or functions in the system. In one embodiment, the RPCs are software modules that perform higher-level functions than the functions performed by the rules-based management kernel. For example, one of the RPCs may be dedicated to performing functions or activities that specifically relate to accounting and billing procedures.

Another RPC may be dedicated to medical record archive and retrieval. Another RPL may perform functions related to insurance authorization, while another RPC may control the acquisition and distribution of medical images and/or lab work performed in the hospital. Still another RPC may be dedicated to exchanging information between the hospital and one or more outside entities, including pharmacies, doctor offices, and other third-party concerns. Still another RPC may be dedicated to registering and authorizing cloud users and controlling communications through the cloud.

Generating higher-level queries is one of the operations that may be performed by the RPCs. The RPCs may generate these higher-level queries and task requests, for example, based rule-operators and/or rule processing logic. The RPCs may interact with the RMBS kernel 420 to interpret and retrieve information to allow the dedicated tasks of the RPCs to be performed.

In operation, parsing logic may be included, first, to determine, the one or more specific RPCs that are to be used in handling a query or perform an activity and, second, to send the query to the one or more relevant RPCs for processing.

The RPCs may operate independently from one another or may operate cooperatively when, for example, an activity to be performed encompasses a plurality of interrelated functions. In accordance with one embodiment, the RPCs may scale automatically depending on the processing load of the system. Also, the functions performed by the RPCs may be synchronized or otherwise managed to cooperate in satisfying the query or requested task.

The modality dictionary 440 stores information including a plurality of modality data models. In one embodiment, the modality dictionary stores information describing modality data and relationships between modality data elements within one or more modality data models. The modality dictionary may also store information linking or otherwise relating the modality data models.

The modality dictionary may be used as a basis for determining the mode of operation or classification of received tasks or queries to be performed by the system. This determination may be made based on information, or the classification of information, received from the work flow management system 470. Once the mode has been classified or determined, one or more RPCs in the rule processing engine may be selected for purposes of processing the task or query.

In one embodiment, the modality dictionary may define the mode of operation of the system when performing cloud-computing operations and/or the transmission or storage of information from cloud users.

Additionally, or alternatively, the modality dictionary may set the context of the system. For example, the modality dictionary may provide for physical and/or logical modality data modeling of healthcare (e.g., hospital, medical, etc.) information as well as in the clinical finding domain. This may involve setting the syntax or semantics to be used by the RQL engine in searching the rules repository in cooperation with information from the rule dictionary.

Concerning the RQL engine, RQL syntax may be based on a combination of RQL keywords. Using RQL syntax, a modality-specific rule semantic may be implemented where rules may be RBMS-specific or RBMS-independent. Also, mapping between rules and modality specific dictionary elements may be performed, for example, by the rules processing engine using, for example, one or more of the RPCs.

In accordance with one embodiment, in addition to the foregoing types of information the rules in the rule repository may include mapping rules for the modality dictionary elements used by the RPCs of the rule processing engine. The mapping rules may be used to construct modality specific data processing initaed in the operating context. The operating context, for example, may represent interfaces and environments for allowing the rules-based management system to communicate with internal and external entities including various servers, databases, computer systems and networks. In accordance with one embodiment (to be discussed in greater detail), the operating context includes a private cloud of different modality-specific data processing artifacts and information.

The work flow management system 470 may operate as a manager and scheduler for sending task requests and queries to the rules-based management system. In performing this function the work flow management system may priority the requests, giving processing preference to higher priority or more urgent requests than others. For example, task requests concerning cardiac patient monitoring and status may be given a higher priority over logistics or inventory ordering requests. The processing results of the rules-based management system may flow through the work flow management system to other parts of the system and/or the processing results may bypass the work flow management system in this regard.

Figure 5:
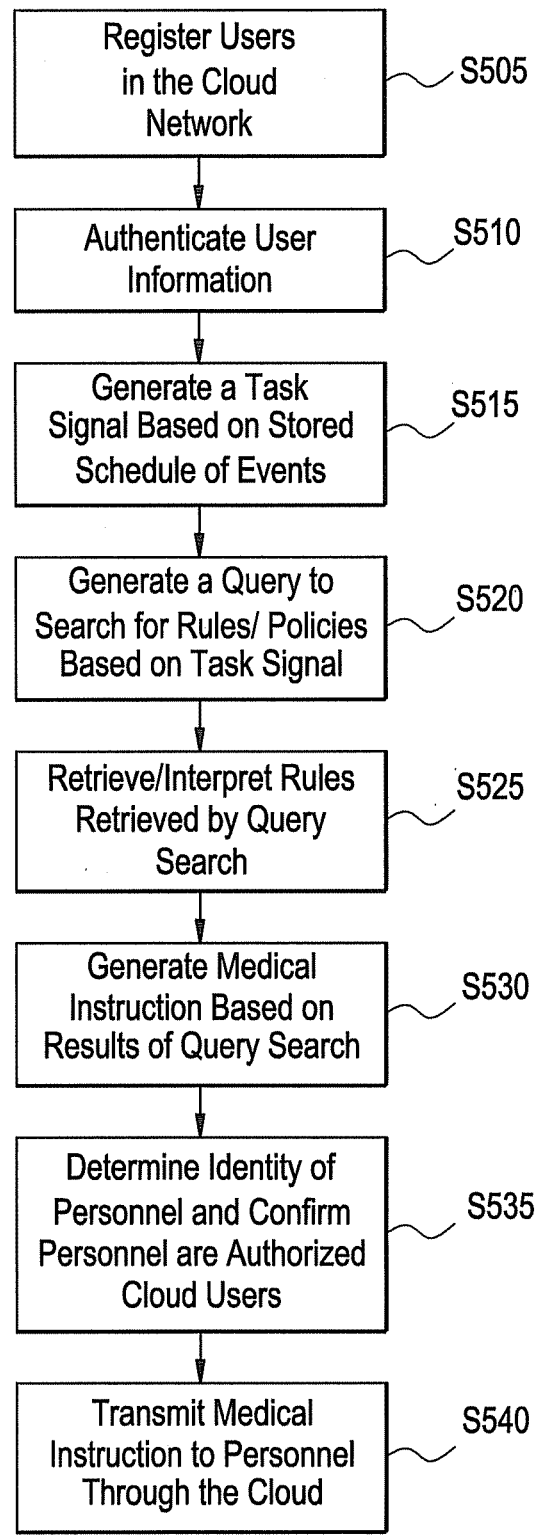
FIG. 5 shows operations included in one embodiment of a rules-based method for managing medical information.

FIG. 5 shows operations included in one embodiment of a method for processing information including medical information. The method will be described based on the use of a cloud network. However, in other embodiments, communication of information may not involve the use of a cloud network, but rather one or a combination of local, wired, wireless or wide area networks including but not limited to a virtual private network. The method may be performed using the systems shown in FIG. 1, 2 or 3 or the arrangement shown in FIG. 4. In alternative embodiments, a different system or arrangement may be used.

Initially, the method includes a number of operations performed during an enrollment procedure. These operations include registering users in the cloud network. (Block S505). This registration may be performed, for example, by having the users enter identification information into a specific website or other network address and/or by otherwise providing this information to authorized network personnel or entity. For example, in the case where a user is a doctor, the identification information may include qualifications and credentials of the doctor, his office information, and various forms of contact information including the terminal(s) to be used in communicating information to and from the cloud.

In the case where the user is a patient, name, address, doctor information, and insurance information may be provided, as well as the terminal(s) to be used in communicating information to and from the cloud. The identification of insurance providers, techniques, administrators and other personnel may be given in like manner.

Once this registration information is received, a set of steps may be taken to authenticate the users. (Block S510). This step may be performed manually in terms of confirming personal licenses and other information. In terms of user terminals, the confirmation of certain qualifying software may be performed including certificates, keys, and encryption software may be performed. The terminals may then be given permissions by the cloud network controller based on the registration and authentication of their users. The use of encryption keys and digital certificates in communicating information provides a further measure of security and privacy of information to be disseminated throughout the system.

Once registered and authenticated, the rules-based management system performs operations based on queries as previously described. These operations may be performed by one or more cloud network controllers, or when a cloud is not included by one or more system processors. In the context of a cloud, the distribution of information may be performed automatically (as defined by one or more rules, policies enforced by the rule dictionary, and/or operational mode of the modality dictionary) by the rules-based management system and/or may be event-driven such as, for example, when tests become available on the network.

Automatic Distribution of Information

Referring to FIG. 5, in this operational mode, the decision to distribute or store information or to perform another cloud or system operation originates with the control software of the rules-based management system and/or the work flow management system. For example, the work flow management system may store a schedule of events to be performed. Based on this schedule, a signal corresponding to a directive, request, or task may be generated for handling by the rules-based management system. (S515).

When the signal is received, the RQL engine of the RMBS kernel may generate a query to search for rules in the rule repository relating to the signal. (S520). This search may be performed with the assistance of the rule dictionary and/or retrieved rules may be interpreted by definitions, policies, and/or other information in the rule dictionary. (S525).

An example of the aforementioned operations includes a schedule of tests to be performed on a patient admitted to a hospital. The schedule may be initially prepared, for example, by a doctor or other medical personnel or an outside doctor, or may be based on insurance company approval. The test may be a diagnostic or exploratory test to be performed prior to surgery or other medical procedure or which is otherwise related to the medical status or condition of the patient. In one scenario, the test may be an electrocardiogram of a patient to receive surgery to implant a pace maker. Another scenario may involve a blood test to be performed prior to surgery to remove or treat a damaged organ. In another scenario, the test may be an imaging test of a patient having a compound fracture or brain surgery.

When a scheduling event is triggered, a query may be generated by the RQL engine to, first, identify the test and, second, to look for rules and policies relating to the implementation of the test. In the case of a cardiac patient, one rule may specific that the test is to be performed a certain number of hours before surgery, another rule may dictate the type of equipment to be used and/or the conditions of the test to be taken.

Based on this information, a corresponding one of the RPCs of the rule processing engine may generate a report, medical instruction, or authorization for the test. (S530). The RPC may also determine, for example, based on information from the modality dictionary, what mode is to be performed for the test. This mode may determine which personnel or department is to receive the instruction. In performing this latter task, the RPC may determine whether the personnel are registered and authorized users of the cloud. (S535).

Once the personnel are confirmed to be authorized users of the cloud, the RPC may transmit the report or instruction to the personnel through the cloud. (Block 540). The transmission of this information may take place unsolicited by the personnel to receive the medical instruction or may be performed in response to a request for the personnel to receive the instruction. The manner in which the communication takes place may be based on the type and/or network architecture of the cloud.

Figure 6:
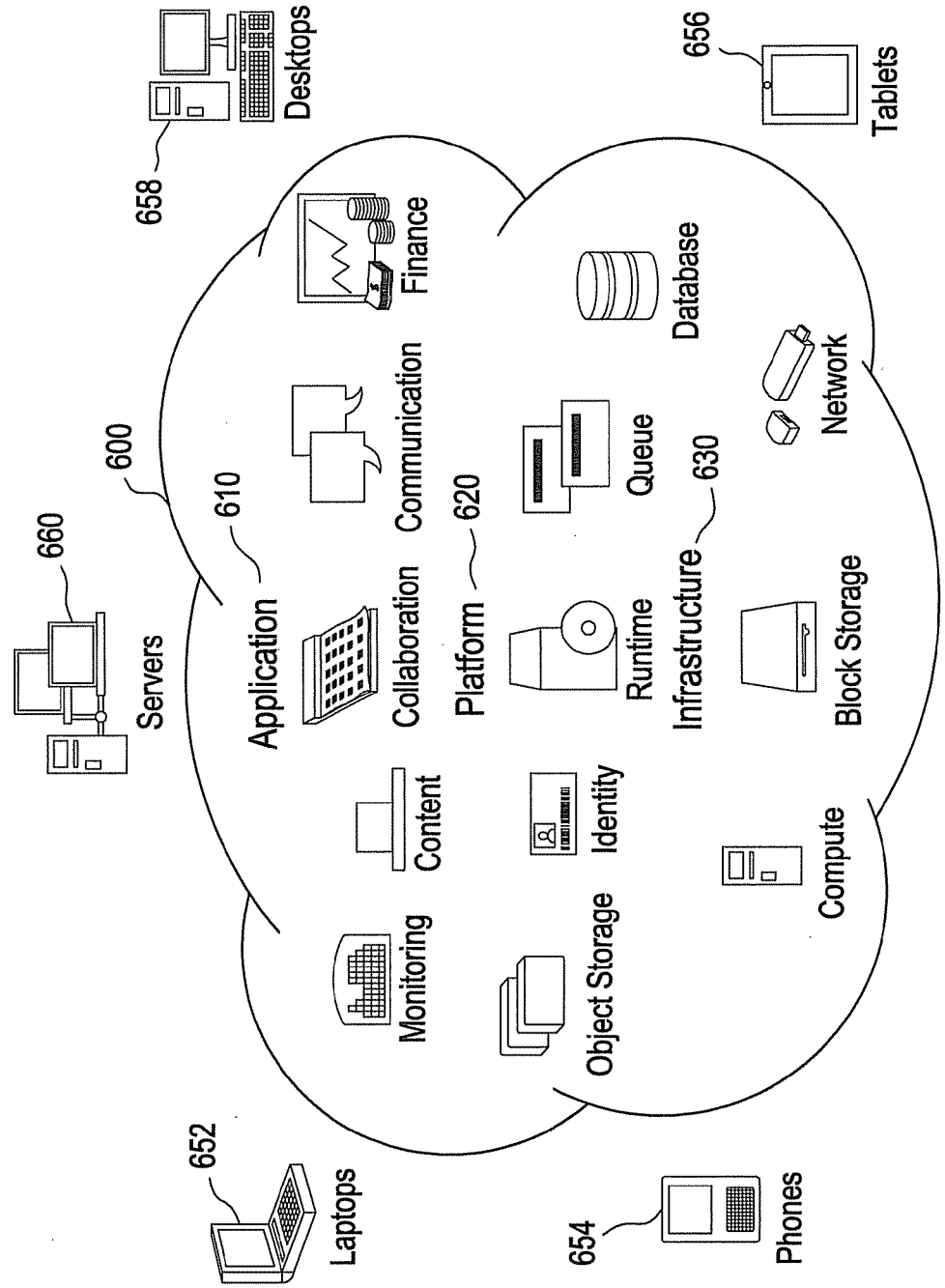
FIG. 6 shows an example of a cloud network in accordance with the rules-based management system and method.

FIG. 6 shows an example of how the cloud may be structured. In this example, the cloud network 600 includes a cloud network storage device that stores a plurality of application programs 610. These programs may include one or more of a monitoring application corresponding to patient status and condition, content information providing specific information relating to the instructions (e.g., timing, duration, type, or other information of a test to be performed), collaboration information identifying which personnel are associated with or are otherwise to be notified of the test, communication information including mobile terminal or other network addresses of the personnel to be notified, and finance information which, for example, may correspond to insurance information and/or authorizations related to the medical instruction. This information may be embedded in the rule repository, rule dictionary, and/or modality dictionary and the application programs may be implemented by one or more RPCs of the rule processing engine.

The cloud network may operate based on a platform 620 which includes one or more devices for storing patient files, identity information for medical personnel and patients, a runtime processor which, for example, may correspond to a cloud network controller or other processor of the rules-based management system, a queue which may store information, instructions, or schedules derived the work flow management system, and a database which may store additional system information.

The cloud network may also include a number of hardware components such as previously discussed. An example of the hardware components includes a computing processor, a block storage device, and a variety of network interfaces. The types of interfaces may be based on the structure of the cloud. In one embodiment, the cloud may transmit information wirelessly within the hospital to one or more user terminals. In FIG. 6, the user terminals are illustratively shown as laptop computers 652, smart phones 654, tablets 656, and desktop work stations 658. In this case, the cloud network may be a wireless private local area network with access points located at various positions throughout the hospital to ensure complete connectivity, irrespective of location.

Figure 7:
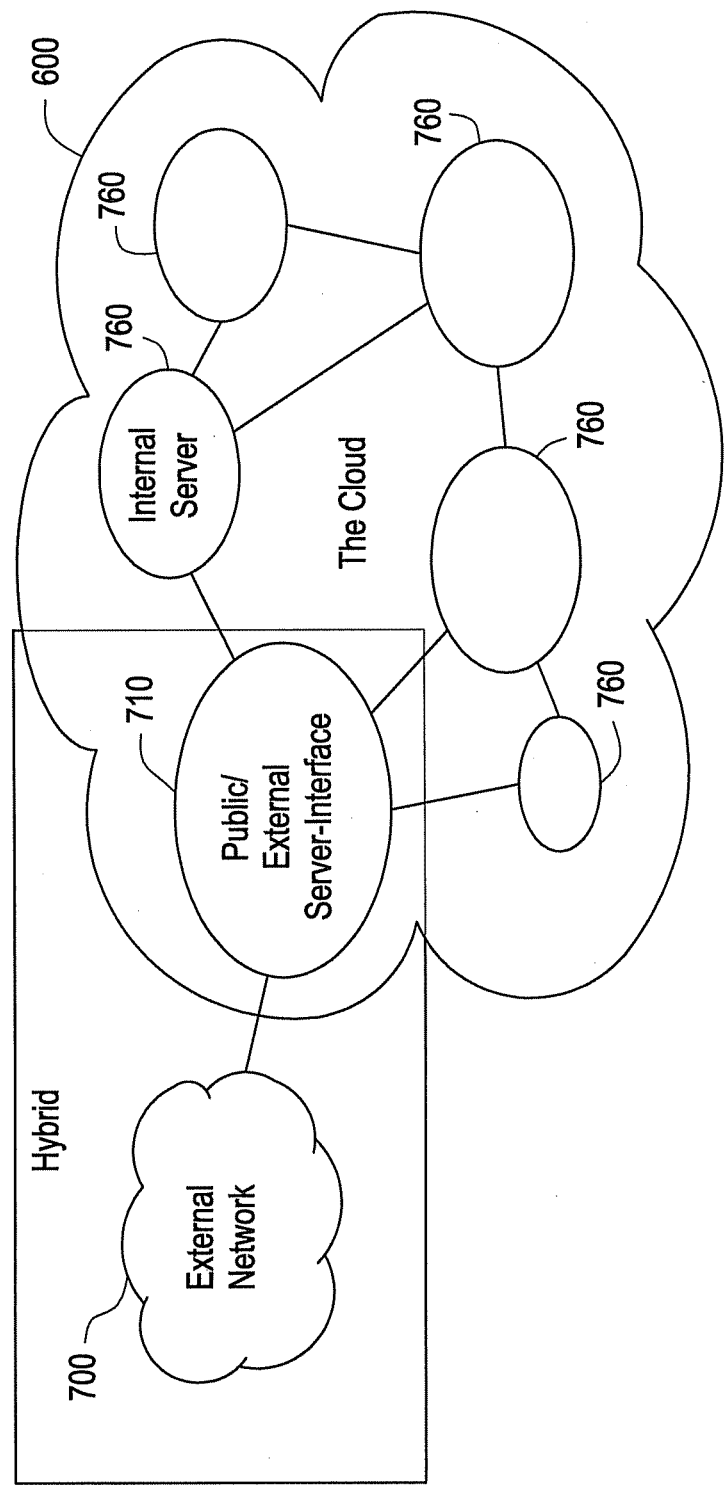
FIG. 7 shows another example of a cloud network in accordance with the rules-based management system and method.

Additionally, or alternatively, the cloud network may include or be formed from one or more hard-wired connections such as a wired local area network. The cloud network may also include one or more servers 660 for linking the hospital network with one or more external networks. As shown in FIG. 7, a public/external server interface 710 may link the cloud network 600 with one or more external networks 700 may include the Internet, a wireless mobile communications network, one or more private networks, another cloud, or a combination of these or other networks or links. The private networks may be networks of a physician's office, pharmacy or insurance company, for example.

The cloud network may also include a number of access points for short-range communication including ones for establishing Bluetooth and Wi-Fi links, as well as ones corresponding to other types of short-range communication protocols. The URL, network addresses, smart phone numbers (e.g., for instant messaging) may be stored in the system for communication with user terminals throughout the cloud network and its external links. The user terminals may be doctor, patient, administrative or third party terminals.

In another application, the schedule may drive the rules-based management system, e.g., through its cloud network controller, to automatically retrieve medical images, record, or past patient history information for transmission to one or more user terminals throughout the cloud network. In terms of storage, while the cloud network may have its own storage coupled to the cloud network controller, additional storage for the cloud network may be shared across the user terminals.

In terms of control software, the user terminals may store applications for interfacing with the cloud and its constituent subsystems/software modules and other cloud users. Additionally, or alternatively, the terminals may store a shell of the application (e.g., application programming interface (API)) with the substantive code being downloaded from an application stored in a cloud management device. The cloud network may therefore include an application server for this purpose.

In addition to these features, the cloud network controller implementing the rules-based management system may perform data backup operations on an intermittent, real-time, or scheduled basis. In this embodiment, the cloud network controller may signal, or "ping," the user terminals to determine whether they have any data to be uploaded to the system. If so, signals may be exchanged to cause the data to be uploaded to the cloud network controller for storage and/or subsequent scheduling of tasks.

Event-Driven Distribution of Information

Figure 8:
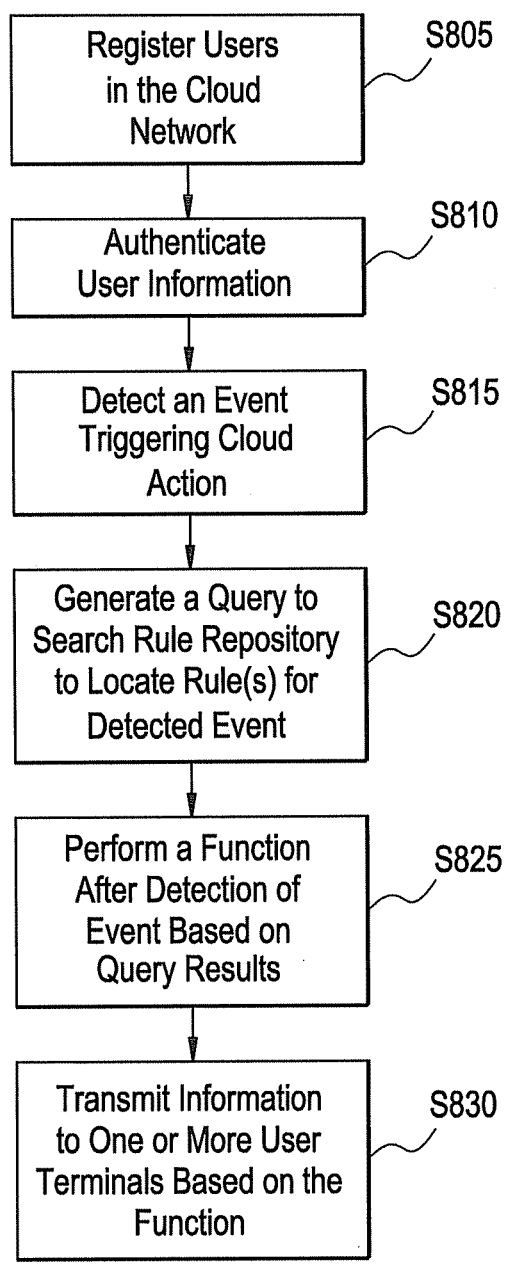
FIG. 8 shows operations included in another embodiment of a rules-based method for managing medical information.

Referring to FIG. 8, in this operational mode, the decision to distribute or store information or to perform another cloud or system operation is based on detection of an event. Thus, the system is responsive to some external signal. Initially, in this mode, users and user terminals are registered (S805) and authenticated (S810) in a similar manner as previously described. Then, an event is detected by the cloud network controller or another network entity. (S815).

The event may be one or more conditions used to notify the system or which otherwise trigger the system to perform an active or passive operation. For example, one trigger includes detection of a user (or more accurately a user terminal) into the hospital. Detection of this event may be performed in a variety of ways including sensors at the hospital entrances, GPS signals, or other tracking data generated, for example, by a network or other application.

When the cloud network controller of the rules-based management system detect this event, a corresponding one of the rule processing engine components (RPCs) directs the RQL engine to search the rule repository with the assistance of the rule dictionary. The RQL engine responds by generating one or more search queries to find rules based on the detection of the user into the hospital. (S820).

Based on the results of this query, the corresponding RPC performs a number of functions based, for example, on information from the modality dictionary. (S825). According to one scenario, after detection of the user terminal in the hospital, the RPC may (through the cloud controller) retrieve a daily schedule for the user. If the user is a doctor, the schedule may be a list of patient appointments, surgeries, diagnostics or patient test results, or meetings.

According to another scenario, the event may be the completion of a test. For example, when the imaging department of the hospital has stored CAT scan, MRI, X-ray or ultrasound images in digital form on a storage device of the hospital, the storage of this information may be an event detected by the rules-based management. In response to detection of this information, the digital imagery may be retrieved from storage. Additionally, or alternatively, the test may be laboratory results for the blood or urine of a patient.

According to another scenario, the event may be detection of a sudden change in patient status. For example, when change of vital signs of a patient is detected by monitoring equipment, a message may be generated to notify the doctor. In the case where the user is a nurse, the message may be generated for the nurse's station.

When the user is a technician or laboratory worker, the event may be entry of doctor orders into the system directing that a specific test be performed. When this event occurs, the rules-based management system may generate a message to notify the technician of this test. Additionally, this notification may be automatically integrated into the technician's schedule, which may prove beneficial when the hospital is crowded.

When the user is a hospital administrator, the event may be the admittance of a patient the hospital. When this occurs, the system may generate information to notify an administrator of the need to contact an insurance company of the patient in question.

After the event has been detected and a corresponding action triggered, the cloud network controller transmits information to the user terminal to notify the user of the specific action. (S830). The user may be located within the hospital or outside the hospital. For example, when a patient has been admitted, information may be automatically transmitted to an insurance company of the patient to notify that company of the admittance and any coverage-related issues.

In the case of a change of status of a patient, the system may automatically transmit a message to a relative of the patient informing the relative of the change of status. Concurrently, a similar message may be sent to a doctor, who may be the attending physician in the hospital and/or the patient's primary care doctor. Records of each of these actions may be automatically archived in system storage for later review.

In another scenario, the event may be storage of a record of a patient prescription. This may trigger automatically sending the prescription to the pharmacy of the patient on record, as a way of expediting convenience to the patient. In another scenario, the event may be receipt of information indicating that a patient is to be released from the hospital. In this case, information may be sent to the attending nurse with orders to give the patient his release papers and any other information the patient may need.

In other scenarios, the event may be receipt of information from a third party or other external source. For example, in the case where a patient received care from a primary physician or had a test performed by an independent laboratory, the physical or laboratory may send this information to the cloud network controller, which then notifies the doctor and sends the test results, lab work, medical images, or other information directly to the user terminal of the doctor for immediate review. This may expedite the care-giving process to the patient, and even in some cases save lives.

While some of the foregoing embodiments may be performed in a hospital, in other embodiments the rules-based management system may be employed in a clinic, doctor's office, laboratory or other setting, with or without interaction with the hospital.

Storage-Driven Distribution of Information

Referring to FIG. 9, in this operational mode, the decision to distribute or store information or to perform another cloud or system operation is based on detection of the storage information in the user terminal. In accordance with one embodiment, a user receives information of a type which is managed by the rules-based management system via the cloud network. (S905).

After this information is received, the information is input for storage into a user terminal. (S910). The user terminal may be the terminal of a doctor, nurse, technician, paramedic, patient, or administrator to name a few. The user terminal is equipped with software which detects the storage of this information. (S915). After storage of this information is detected in the terminal, the control software in the terminal automatically establishes a connection with the cloud network controller or one of its constituted processors, servers, or other elements. (S920).

Once this connection is established, the terminal automatically transmits the stored information to the cloud network controller. (S925). Thus, the act of storing information using a specific application on the user terminal may constitute the trigger for causing the terminal software to automatically transmit that stored information to the cloud network controller. This may take place transparently to the user or the user may otherwise be notified that transmission of the information has been successfully performed.

When the network cloud controller receives this information, the controller may respond with additional information. For example, in the case where a diabetic patient has stored a blood glucose reading in his smart phone, an application in the smart phone may automatically transmit information including the reading to a doctor. The rules-based management system implemented by the cloud network controller may then transmit information back to the patient suggesting specific times for appointments or further instructions on how to proceed given the reading.

When the user terminal receives the transmitted information, it may update a user's schedule application and/or may otherwise output a notification on the terminal (S930). Additional information and/or signals may be exchanged triggered, for example, by the storage of additional information in the user terminal.

In addition to the aforementioned embodiments, one implementation of the system and method allows for the formation of scripting tasks to change or update the functionary of the rules-based management system software modules. Scripting task capability also allows for reconstructing process flow and management control on some other compatible platform.

In accordance with one or more embodiments, the rules-based management system allows for enhanced capability relating to medical- and/or hospital-related information management provided using a virtual machine, a knowledge system, an expert system, or other form of artificial intelligence. In one embodiment, the delivery of clinical information and rules for processing that information is provided for activity in an integrated medically related environment.

The system may also eliminate waste and delays related to information management, which at the very least will improve efficient of information distribution to heath care professionals and improve the rate of patient recovery or even survival. The system also offers doctors a valuable analytical tool in reviewing in real-time or near real time test and medical imaging results, thereby speeding the flow of patient care through the hospital, clinic or doctor office. These and other improvements may be achieved using a cloud-based network that may operate transparently to system users, thereby further improving efficiency.

In accordance with another embodiment, a computer-readable medium stores code or other instructions for implementing operations of the aforementioned methods. The medium may be a hard-disk driven, a storage chip, a database, a memory, or a compact or digital versatile disk. The medium may also be information downloaded to a user terminal or controller through the Internet or another network.

In accordance with one embodiment, a rules-based management system includes a rule repository to store rules relating to medical information, a rule query language engine to generate a query based on a received signal and to search the rule repository based on the query, a rule processing engine to formulate an instruction based on one or more rules produced by the search of the rule repository and to generate a signal based on the instruction, and an interface to a cloud network. The interface is configured to send the signal to the cloud network to enable performance of a task related to the medical information.

The system may further include a manager to detect an item on a schedule and the rule query language engine may automatically generate the query after detection of the item on the schedule. The schedule may be a doctor schedule.

The system may further include a manager to detect an event and the rule query language engine may automatically generate the query after detection of the event. The event may include performance or results of medical imaging, a laboratory test, a change in a condition of a patient, an insurance approval or submission of a procedure for a patient, an emergency condition, or a detected location of a doctor or patient.

The system may further include a receiver to receive a signal indicating availability of data and the rule query language engine may automatically generate the query after receipt of the signal. The signal may be a user terminal signal.

The system may further include a rule dictionary configured to store information relating to the rules in the rule repository. The rule query language engine may search the rule repository based on information from rule dictionary.

The system may further include a cloud network controller to determine one or more user terminals to receive the signal through the interface connected to the cloud network.

The system may further include a modality dictionary to store information corresponding to different modes of operation for different queries, and the rule processing engine may formulate the instruction based on the one or more rules and the information from the modality dictionary.

In accordance with another embodiment, a method for processing information includes generating a query for a rule repository, searching the rule repository based on the query to locate one or more rules relating to medical information, formulating an instruction based on the one or more rules, generating a signal to perform a task based on the instruction, and establishing a connection with a cloud network for transmission of the signal, wherein the task corresponds to medical action to be performed in a hospital.

The method may further include detecting an item on a schedule, wherein the query is automatically generated after detection of the item on the schedule. The schedule may be a doctor schedule.

The method may further include detecting an event and the query may be automatically generated after detection of the event. The event may include performance or results of medical imaging, a laboratory test, a change in a condition of a patient, an insurance approval or submission of a procedure for a patient, an emergency condition, or a detected location of a doctor or patient.

The method may further include receiving a signal indicating availability of data, wherein the query is automatically generated after receipt of the signal. The signal may be a user terminal signal.

The method may further include receiving information from a rule dictionary, wherein searching the rule repository is performed based on the query and the information from the rule dictionary.

The method may further include determining one or more user terminals to receive the signal through the connection to the cloud network.

The method may further include receiving information from a modality dictionary, wherein formulating the instruction includes formulating the instruction based on the rules and information from the modality dictionary.

While example embodiments are capable of various modifications and alternative forms, the embodiments are shown by way of example in the drawings and will be described herein in detail. It should be understood, however, that there is no intent to limit example embodiments to the particular forms disclosed. On the contrary, example embodiments are to cover all modifications, equivalents, and alternatives falling within the scope of this disclosure. Like numbers refer to like elements throughout the description of the figures.

Although the terms first, second, etc. may be used herein to describe various elements, these elements should not be limited by these terms. These terms are only used to distinguish one element from another. For example, a first element could be termed a second element, and similarly, a second element could be termed a first element, without departing from the scope of this disclosure. As used herein, the term "and/or," includes any and all combinations of one or more of the associated listed items.

When an element is referred to as being "connected," or "coupled," to another element, it can be directly connected or coupled to the other element or intervening elements may be present. By contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of example embodiments and corresponding detailed description are presented in terms of algorithms performed by a controller. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

Specific details are provided in the following description to provide a thorough understanding of example embodiments. However, it will be understood by one of ordinary skill in the art that example embodiments may be practiced without these specific details. For example, systems may be shown in block diagrams so as not to obscure the example embodiments in unnecessary detail. In other instances, well-known processes, structures and techniques may be shown without unnecessary detail in order to avoid obscuring example embodiments.

In the following description, illustrative embodiments will be described with reference to acts and symbolic representations of operations (e.g., in the form of flow charts, flow diagrams, data flow diagrams, structure diagrams, block diagrams, etc.) that may be implemented as program modules or functional processes include routines, programs, objects, components, data structures, etc., that perform particular tasks or implement particular abstract data types and may be implemented using existing hardware at existing network elements, existing end-user devices and/or post-processing tools (e.g., mobile devices, laptop computers, desktop computers, etc.). Such existing hardware may include one or more Central Processing Units (CPUs), digital signal processors (DSPs), application-specific-integrated-circuits, field programmable gate arrays (FPGAs) computers or the like.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Although a flow chart may describe the operations as a sequential process, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

Note also that the software implemented aspects of example embodiments are typically encoded on some form of tangible (or recording) storage medium or implemented over some type of transmission medium. As disclosed herein, the term "storage medium" may represent one or more devices for storing data, including read only memory (ROM), random access memory (RAM), magnetic RAM, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, a processor or processors will perform the necessary tasks.

A code or code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

As used herein, the term "terminal" may be synonymous to a mobile user, mobile station, mobile terminal, user, subscriber, wireless terminal, user equipment and/or remote station and may describe a remote user of wireless resources in a wireless communication network. Accordingly, terminal may be a wireless phone, wireless equipped laptop, wireless equipped appliance, etc.

The term "base station" may be understood as a one or more cell sites, base stations, nodeBs, enhanced NodeBs, access points, and/or any terminus of radio frequency communication. Although current network architectures may consider a distinction between mobile/user devices and access points/cell sites, the example embodiments described hereafter may generally be applicable to architectures where that distinction is not so clear, such as ad hoc and/or mesh network architectures, for example.

Communication from the base station to the terminal is typically called downlink or forward link communication. Communication from the terminal to the base station is typically called uplink or reverse link communication.

Example embodiments being thus described, it will be obvious that the same may be varied in many ways. Such variations are not to be regarded as a departure from the spirit and scope of example embodiments, and all such modifications as would be obvious to one skilled in the art are intended to be included within the scope of the claims.

What is claimed is:

1. A rules-based management system comprising:
a rule repository configured to store a plurality of rules relating to medical information;
a rule query language engine configured to generate a query based on a received signal and to search the rule repository based on the query;
a rule processing engine configured to formulate an instruction based on one or more rules produced by the search of the rule repository and to generate a signal based on the instruction;
an interface to a cloud network, wherein the interface is configured to send the signal to the cloud network to enable performance of a task related to the medical information; and
a modality dictionary configured to store first information corresponding to different modes of operation for different queries, and store second information describing modality data and relationships between modality data elements within one or more modality data models, wherein the rule processing engine is configured to formulate the instruction based on the one or more rules, the first information, and the second information.

2. The system of claim 1, further comprising:
a manager configured to detect an item on a schedule,
wherein the rule query language engine is configured to automatically generate the query after detection of the item on the schedule.

3. The system of claim 2, wherein the schedule is a doctor schedule.

4. The system of claim 1, further comprising:
a manager configured to detect an event,
wherein the rule query language engine is configured to automatically generate the query after detection of the event.

5. The system of claim 4, wherein the event includes performance or results of medical imaging, a laboratory test, a change in a condition of a patient, an insurance approval or submission of a procedure for a patient, an emergency condition, or a detected location of a doctor or patient.

6. The system of claim 1, further comprising:
a receiver configured to receive a signal indicating availability of data,
wherein the rule query language engine is configured to automatically generate the query after receipt of the signal.

7. The system of claim 6, wherein the signal is a user terminal signal.

8. The system of claim 1, further comprising:
a rule dictionary configured to store information relating to the rules in the rule repository, wherein the rule query language engine is configured to search the rule repository based on information from rule dictionary.

9. The system of claim 1, further comprising:
a cloud network controller configured to determine one or more user terminals to receive the signal through the interface connected to the cloud network.

10. A method for processing information, comprising:
generating a query for a rule repository;
searching the rule repository based on the query to locate one or more rules relating to medical information;
formulating an instruction based on the one or more rules;

generating a signal to perform a task based on the instruction;

establishing a connection with a cloud network for transmission of the signal, wherein the task corresponds to medical action to be performed in a hospital; and receiving first information and second information from a modality dictionary, the first information corresponding to different modes of operation for different queries, the second information describing modality data and relationships between modality data elements within one or more modality data models, wherein the formulating includes formulating the instruction based on the one or more rules, the first information, and the second information.

11. The method of claim 10, further comprising:
detecting an item on a schedule,
wherein the query is automatically generated after detection of the item on the schedule.

12. The method of claim 11, wherein the schedule is a doctor schedule.

13. The method of claim 10, further comprising:
detecting an event,
wherein the query is automatically generated after detection of the event.

14. The method of claim 13, wherein the event includes performance or results of medical imaging, a laboratory test, a change in a condition of a patient, an insurance approval or submission of a procedure for a patient, an emergency condition, or a detected location of a doctor or patient.

15. The method of claim 10, further comprising:
receiving a signal indicating availability of data,
wherein the query is automatically generated after receipt of the signal.

16. The method of claim 15, wherein the signal is a user terminal signal.

17. The method of claim 10, further comprising:
receiving information from a rule dictionary,
wherein searching the rule repository is performed based on the query and the information from the rule dictionary.

18. The method of claim 10, further comprising:
determining one or more user terminals to receive the signal through the connection to the cloud network.

* * * * *